United States Patent
Obatake et al.

(10) Patent No.: US 12,109,314 B2
(45) Date of Patent: Oct. 8, 2024

(54) SOFT CAPSULE FILM COMPOSITION

(71) Applicant: FUJI CAPSULE CO., LTD., Shizuoka (JP)

(72) Inventors: Yuki Obatake, Shizuoka (JP); Yosuke Kondo, Shizuoka (JP); Koji Masuda, Shizuoka (JP); Kazuhiko Watanabe, Shizuoka (JP); Yoshihiko Watanabe, Shizuoka (JP)

(73) Assignee: FUJI CAPSULE CO., LTD., Shizuoka (JP)

( * ) Notice: Subject to any disclaimer, the term of this patent is extended or adjusted under 35 U.S.C. 154(b) by 0 days.

(21) Appl. No.: 17/049,095

(22) PCT Filed: Apr. 24, 2019

(86) PCT No.: PCT/JP2019/017529
§ 371 (c)(1),
(2) Date: Oct. 20, 2020

(87) PCT Pub. No.: WO2019/208668
PCT Pub. Date: Oct. 31, 2019

(65) Prior Publication Data
US 2021/0196641 A1  Jul. 1, 2021

(30) Foreign Application Priority Data
Apr. 26, 2018 (JP) ................. 2018-085156

(51) Int. Cl.
*A61K 9/48* (2006.01)
*A61K 47/36* (2006.01)

(52) U.S. Cl.
CPC ............ *A61K 9/4816* (2013.01); *A61K 47/36* (2013.01)

(58) Field of Classification Search
CPC .............................. A61K 9/4816; A61K 47/36
See application file for complete search history.

(56) References Cited

U.S. PATENT DOCUMENTS

2016/0175258 A1* 6/2016 Kato .................... A61K 8/732
                                                                428/402.2
2017/0292011 A1* 10/2017 Watanabe ............... C08L 5/00

FOREIGN PATENT DOCUMENTS

| | | |
|---|---|---|
| JP | 2003-504326 A | 2/2003 |
| JP | 2005170929 A | 6/2005 |
| JP | 2006299052 A | 11/2006 |
| JP | 2007153851 A | 6/2007 |
| JP | 2007153889 A | 6/2007 |
| JP | 3990741 | 7/2007 |
| JP | 2009040716 A | 2/2009 |
| JP | 4959948 | 6/2012 |
| JP | 5149465 B2 | 2/2013 |
| JP | 2013040217 A | 2/2013 |
| JP | 5226281 | 7/2013 |
| JP | 5688193 | 3/2015 |
| JP | 2015059106 A | 3/2015 |
| JP | 5923029 B2 | 5/2016 |
| JP | 2017-31134 A | 2/2017 |
| JP | 2017-105829 A | 6/2017 |
| JP | 2017114790 A * | 6/2017 |
| WO | 2015008748 A1 | 1/2015 |
| WO | 2016052699 A1 | 4/2016 |
| WO | 2017/022230 A1 | 2/2017 |

* cited by examiner

*Primary Examiner* — Susan T Tran
*Assistant Examiner* — William Craigo
(74) *Attorney, Agent, or Firm* — Edwin S. Flores; Daniel J. Chalker; Chalker Flores, LLP (57) ABSTRACT

A soft capsule film composition, comprising: (A) a native gellan gum; (B) one or more hydrophilic polysaccharides; (C) a starch or modified starch; (D) a plasticizer; and (E) water, wherein a gelling agent other than the native gellan gum and the one or more hydrophilic polysaccharides is not an essential component. The soft capsule film composition shortens drying time at room temperature, suppresses the stickiness of the surface of a film sheet, imparts film sheet strength which can withstand continuous production in factory manufacturing with a rotary die filling machine or the like, and enables the manufacture of a good soft capsule with high adhesiveness. For this reason, the soft capsule produced using the soft capsule film composition can be utilized for various uses such as drugs, quasi drugs, cosmetics, and foods.

9 Claims, 1 Drawing Sheet

SOFT CAPSULE FILM COMPOSITION

CROSS-REFERENCE TO RELATED APPLICATIONS

This application is the National Stage of International Application No. PCT/JP2019/017529, filed on Apr. 24, 2019 claiming the priority of JP 2018-085156, filed on Apr. 26, 2018, the content of each of which is incorporated by reference herein.

TECHNICAL FIELD

The present invention relates to a soft capsule film composition, and a soft capsule film and a soft capsule using the same.

BACKGROUND ART

Figure 1:
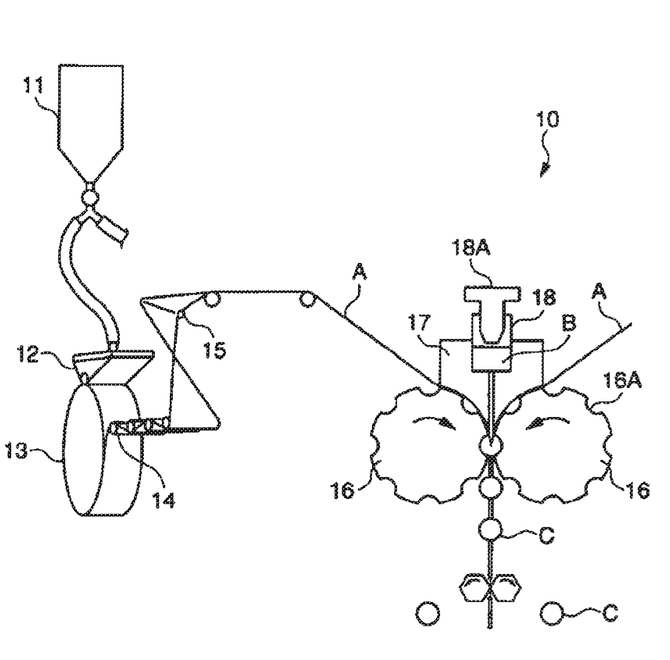
FIG. 1 is a schematic diagram showing a rotary die capsule filling machine.

In a rotary die filling method, which is one of the methods for producing a soft capsule, as shown in FIG. 1, a solution of a film composition is spread on cooled rotary drums on both sides of a capsule filling machine and formed into a sheet shape, its film sheet is fed between rotating cylindrical metallic molds (die rolls), and the contents are injected with the piston of a pump interlocked with this to form a capsule by press-cutting with both metallic molds. At this time, the film sheets are heated to a suitable temperature with segments and adhered by pressure and heat sealing to become a soft capsule.

Properties required for a film composition to be subjected to molding by this process are mechanical strength which enables withstanding continuous steps from the molding of a film sheet to filling and sol-gel thermal reversibility for heat sealing or adhesiveness by crimping. Gelatin, which combines these characteristics on a high level as a soft capsule film composition, was used in the past.

Meanwhile, a nonanimal soft capsule film composition substituted for gelatin, which is mainly produced from bones and skin of bovines, swine or the like as raw materials, has been desired for fear of BSE (bovine spongiform encephalopathy) problems, religious reasons, allergies, or the like in recent years. Various soft capsule film compositions using seaweed polysaccharides such as agar and carrageenan (Patent Document 1) have been proposed as substitutes for gelatin. Besides, as seen in Patent Documents 2 to 13, soft capsule film compositions using nonanimal materials including gellan gum, which is a polysaccharide produced by microorganisms, as gelling agents have also been proposed.

Various starches are used when soft capsule films are produced. Natural starches and various modified starches have been used until now. Examples of natural starches include potato starch, tapioca starch, sago starch, sweet potato starch, mung bean starch, wheat starch, corn starch, rice starch, waxy corn starch, waxy potato starch, waxy wheat starch and waxy rice starch. Examples of modified starches include starches obtained by subjecting the above-mentioned natural starches to acetylation, hydroxypropylation, octenylsuccination, phosphorylation, crosslinking, acid treatment, moist heat treatment, or ultrasonic treatment (especially Patent Documents 13 to 14).

PRIOR ART DOCUMENTS

Patent Documents

Patent Document 1: Japanese Unexamined Patent Application Publication (Translation of PCT Application) No. 2003-504326
Patent Document 2: Japanese Patent No. 3990741
Patent Document 3: Japanese Unexamined Patent Application Publication No. 2005-170929
Patent Document 4: Japanese Patent No. 4959948
Patent Document 5: Japanese Unexamined Patent Application Publication No. 2006-299052
Patent Document 6: Japanese Unexamined Patent Application Publication No. 2007-153851
Patent Document 7: Japanese Unexamined Patent Application Publication No. 2007-153889
Patent Document 8: Japanese Patent No. 5226281
Patent Document 9: Japanese Unexamined Patent Application Publication No. 2009-040716
Patent Document 10: Japanese Patent No. 5688193
Patent Document 11: Japanese Patent No. 5149465
Patent Document 12: Japanese Patent No. 5923029
Patent Document 13: International Publication No. WO 2016/052699
Patent Document 14: Japanese Unexamined Patent Application Publication No. 2015-059106

SUMMARY OF THE INVENTION

Problems to be Solved by the Invention

Gellan gum attracts attention as a polysaccharide having the effect of forming gel other than carrageenan derived from seaweed. Gellan gum includes native gellan gum (also called "native type gellan gum", "highly acylated gellan gum" or "HA gellan gum") and deacylated gellan gum (also called "deacylated type gellan gum" or "LA gellan gum").

However, the following problems remain in the production of a soft capsule film composition using gellan gum, and its soft capsule.

In a conventional soft capsule film composition, the use of native gellan gum alone or a mixture of native gellan gum and deacylated gellan gum, or native gellan gum and other natural polymer gelling agents such as agar or carrageenan in combination together with starch and a plasticizer forms the soft capsule film composition. The problem is, however, that in film sheets consisting of starch utilizing native gellan gum as the main gelling agent, front surfaces of the sheets out of contact with rotary drums are generally sticky as compared with the reverse surfaces, which are in contact with the rotary drums, and when the production with the above-described rotary die filling machine, which is widely utilized as an existing soft capsule producing device, is attempted, the front surfaces of the sticky film sheets adhere to the rotating die rolls, and the encapsulation is impossible; or the adhesion is weak, and continuous molding can hardly be performed even though the contents are enclosed barely. A rotary die filling machine is subjected to device design so that the machine is suitable to the filling molding of a soft capsule consisting of a gelatin film, in which the reverse surface which is stickier oppositely to the film sheet utilizing native gellan gum. When the practical use of the existing rotary die filling machine without extensive conversion of equipment or the like produces the soft capsule using native gellan gum, this point can be a serious problem. When carrageenan and native gellan gum are used together as gelling agents, the physical properties of a film have defects, and it is also indicated that the film is inferior in elasticity and adhesive properties after encapsulation as compared with when carrageenan alone is used (Patent Document 11 and the paragraph of Patent Document 12).

Note that the following facts can be considered as reasons the film sheet consisting of native gellan gum and starch exhibits such properties. That is, the gelling temperature of the film sheet using native gellan gum is considerably high as compared with gelatin or the like. Therefore, when the film sheet is formed on the rotary drum of the rotary die filling machine, places in which the gelling proceeds and places in which the gelling is slightly late are produced near the front surface of the film sheet by rapid air cooling at room temperature, the gelling state of the sheet becomes ununiform and insufficient, and the sheet becomes sticky gel. Meanwhile, it is considered that air cooling has less influence on the surface of the inside (reverse surface) of the film, which is in contact with the rotary drum than on the front surface, there is also heating from the drum, gel is gelated slowly and uniformly, and a sheet surface which is firm and less sticky is formed.

Also in the case of the film sheet consisting of native gellan gum, deacylated gellan gum, and starch, the film strength does not reach the mechanical strength which enables withstanding continuous production depending on prescription, and the film sheet may rupture during a capsule filling step; or the inconvenience may also occur in that the adhesive strength at the time of crimping is low, and good adhesiveness cannot be obtained.

The fact that gellan gum is a gelling agent with high viscosity as compared with gelling agents which are gelatin and other vegetable polysaccharides, and in the production of a soft capsule film composition using gellan gum, when gellan gum and starch are mixed and dissolved by heating to prepare the film composition, the composition has very high viscosity, the operability at the time of capsule production (homogeneously mixing operability for mixing the composition homogeneously) deteriorates extremely, and a desired concentration is hardly obtained is mentioned. Especially the composition has a problem in that although the solid concentration needs to be increased from the viewpoint of film strength especially at the time of production of a soft capsule, when the concentration is increased, the viscosity of a composition solution increases, and the operability therefore deteriorates, and additionally, in the case of manufacturing on an industrial scale, the machinery and equipment need to be changed on a large scale.

Blocking is a phenomenon frequently seen in a conventional capsule film using gelatin as the main raw material, and the solution to this problem has also been desired strongly.

The present invention has been completed in view of the above-mentioned problems, and is a soft capsule film composition using gellan gum, which is derived from a nonanimal raw material. An object is to steadily produce a soft capsule wherein the stickiness of the front surface of a film sheet is reduced, the mechanical strength of the film sheet is increased to make ruptures and the like hardly occur, and the soft capsule has good adhesiveness by crimping in the industrial manufacturing of the soft capsule including the utilization of an existing soft capsule filling production device such as a rotary die filling machine.

Means to Solve the Problems

The present inventors have extensively repeated investigation to solve the problems and consequently found that if a composition containing (A) native gellan gum, (B) one or more hydrophilic polysaccharides, (C) starch or modified starch, (D) a plasticizer, and (E) water is used, a capsule film wherein the film sheet strength is high, the bite of a film base material into a joint is suppressed, and good adhesiveness is exhibited is obtained without requiring any carrageenan. It has been further found that if the composition is used, excellent film performance such as blocking resistance, elasticity, transparency and rapid disintegration properties is obtained after encapsulation. The present invention has been completed based on these findings.

That is, the present invention relates to the followings.

(1) A soft capsule film composition, comprising: (A) native gellan gum; (B) one or more hydrophilic polysaccharides; (C) starch or modified starch; (D) a plasticizer; and (E) water, wherein a gelling agent other than (A) the native gellan gum and (B) the one or more hydrophilic polysaccharides is not an essential component.

(2) The soft capsule film composition of (1), wherein (C) the starch or the modified starch is one or more starches selected from a natural starch, an oxidized starch, a hydroxypropylated starch, an acetylated starch, starches subjected to acetylation, hydroxypropylation, octenylsuccination, phosphorylation, crosslinking, acid treatment, and moist heat treatment in the presence of a salt, and a starch dispersion obtained by ultrasonically treating a starch paste solution.

(3) The soft capsule film composition of (1) or (2), wherein (C) the starch or the modified starch is one or more starches selected from sago starch, sweet potato starch, mung bean starch, wheat starch, corn starch, rice starch, waxy corn starch, waxy potato starch, waxy wheat starch, waxy rice starch, and modified starches obtained therefrom.

(4) The soft capsule film composition of any one of (1) to (3), wherein (C) the starch or the modified starch is one or more starches selected from waxy potato starch, an oxidized starch, a starch subjected to moist heat treatment in the presence of a salt, and a starch dispersion formed by subjecting the starch glue solution to ultrasonic treatment.

(5) The soft capsule film composition of any one of (1) to (4), wherein a content mass ratio of (A) the native gellan gum to (B) the one or more hydrophilic polysaccharides [(A):(B)] is 1:1 to 1:0.01.

(6) The soft capsule film composition of any one of (1) to (5), wherein the starch dispersion formed by subjecting the starch glue solution to ultrasonic treatment is a starch dispersion derived from waxy corn starch.

(7) The soft capsule film composition of (6), wherein the waxy corn starch used for the starch dispersion formed by subjecting a starch glue solution to ultrasonic treatment is an unmodified natural starch.

(8) The soft capsule film composition of any one of (1) to (5), wherein (C) the starch or the modified starch is waxy corn starch subjected to moist heat treatment in the presence of a salt.

(9) A soft capsule film, wherein the soft capsule film is obtained using the soft capsule film composition of any one of (1) to (8).

(10) A soft capsule, wherein the soft capsule is obtained using the soft capsule film composition of any one of (1) to (8).

Effect of the Invention

Although a soft capsule film composition of the present invention does not contain carrageenan, the soft capsule film composition of the present invention enables shortening drying time at room temperature, suppressing the stickiness of the front surface of a film sheet, imparting film sheet strength which enables withstanding continuous production in factory manufacturing with a rotary die filling machine or the like, and manufacturing a good soft capsule film with high adhesiveness in combination of native gellan gum, one or more hydrophilic polysaccharides, and specific starch or modified starch.

MODE OF CARRYING OUT THE INVENTION

A soft capsule film composition of the present invention is used for a film of a soft capsule utilized for drugs, quasi drugs, foods, health foods, cosmetics and the like, and contains at least native gellan gum, one or more hydrophilic polysaccharides, starch or modified starch, a plasticizer, and water. That is, minimum components required for the soft capsule film composition of the present invention are (A) native gellan gum, (B) one or more hydrophilic polysaccharides, and (C) starch or modified starch. In the soft capsule film composition of the present invention, the content mass ratio of native gellan gum to one or more hydrophilic polysaccharides is 1:1 to 1:0.01.

Gellan gum is a heteropolysaccharides which a microorganism called *Pseudomonas elodea* produces out of bacterial cells, four sugars which are 1,3-linked glucose, 1,4-linked glucuronic acid, 1,4-linked glucose, and 1,4-linked rhamnose form repeat units, and gellan gum has the repeat units bound linearly. Among types of gellan gum, gellan gum in which acyl groups are not bound to the above-mentioned sugars constituting the polysaccharide is generally called deacylated gellan gum, and generally has the property of forming hard fragile gel. Meanwhile, gellan gum in which acetyl groups and glyceryl groups are bound to the glucose forming a 1,3-linked in the repeat units is generally called native gellan gum, and has the property of forming soft stretchy gel. Examples of the native gellan gum include the trade names "KELCOGEL CG-HA", "KELCOGEL LT100", "KELCOGEL HM" and "KELCOGEL HT", and examples of the deacylated gellan gum include the trade names "KELCOGEL" and "KELCOGEL F" (all are provided by CP Kelco Japan). Gellan gum has high heat resistance and forms strong gel as compared with gelling agents such as carrageenan and agar derived from seaweed.

Note that the "gelling agent" mentioned herein means a chemical substance which gelates a liquid sol. The "gelling" means the phenomenon in which a liquid sol solidifies in the shape of jelly. Examples include a gelling agent such as agar or gelatin which gels by cooling and a gelling agent such as an alginate which gels in the presence of specific ions.

In the native gellan gum mentioned herein, acetyl groups and glyceryl groups do not need to be bound to the glucose molecules of all the repeat units. All gellan gums having acylated groups in the whole gellan gum are included in the native gellan gum mentioned in the present invention. In other words, gellan gum in which "the degree of acylation: 0" is "deacylated gellan gum", and all the other types of gellan gum (the degrees of acylation are not 0) is "native gellan gum". The native gellan gum mentioned herein means gellan gum in which the degree of acylation is not 0. Here, "the degree of acylation" can be measured by the ratio of the signal strength of a peak derived from the methyl group of rhamnose which appears near 1.3 ppm to the signal strength of a peak of an acetyl group bound to the hydroxyl group at the sixth position of β-glucose and appears near 2.1 ppm by $^1$HNMR measurement using Bruker Avance DRX-400 (Bruker Japan K.K.). (Nobuki Ando, "Native Gellan no Gel-ka Kiko ni Kansuru Kisokenkyuu (Basic research of Gelling mechanism of Native Gellan)" Tokyo University of Marine Science and Technology, September 2009)

The reasons why native gellan gum was adopted as the gellan gum used in the present invention are as follows.

(1) When deacylated gellan gum is markedly used to produce a soft capsule, the gel is hard, and deacylated gellan gum therefore leads to the deterioration of quality.

(2) Gel of native gellan gum has flexibility and is suitable to produce a soft capsule.

Hydrophilic polysaccharides in the present invention mean water-soluble polysaccharides except native gellan gum. That is, hydrophilic polysaccharides in the present invention refer to polysaccharides which dissolves in water (regardless of temperature). Examples of such hydrophilic polysaccharides include a pectin (a low methoxy pectin (LM pectin) or a high methoxy pectin (HM pectin)); locust bean gum; glucomannan; xanthan gum; carrageenan; furcellaran; deacylated gellan gum; chondroitin and a sulfate thereof; alginic acid and an alginate; an alginic acid derivative such as propylene glycol alginate; a gum-based polymer compound such as gum arabic, guar gum, and tamarind gum; carboxymethyl cellulose; hydroxypropyl starch; pregelatinized starch; pullulan; a hydroxyalkyl cellulose; polyvinylpyrrolidone; polyvinyl alcohol; and agar.

The low methoxy pectin (LM pectin) means a pectin having a degree of esterification (DE) of less than 50%, and the high methoxy pectin means a pectin having a degree of esterification (DE) of 50% or more. Note that the degree of esterification means the ratio of methyl-esterified galacturonic acid molecules to the total galacturonic acid molecules, and can be calculated as a value (%) obtained by dividing the number of methyl-esterified galacturonic acid molecules by the number of the total galacturonic acid molecules and multiplying the divided value by 100.

In the present invention, the content mass ratio of native gellan gum to one or more hydrophilic polysaccharides is preferably 1:1 to 1:0.01, more preferably 1:0.8 to 1:0.03, and further preferably 1:0.6 to 1:0.05.

The content of the hydrophilic polysaccharides is preferably 0.1% by mass or more, and more preferably 0.5% by mass or more in the total amount of solid components from the viewpoint gelling ability. The content of the hydrophilic polysaccharides is preferably 10% by mass or less, more preferably 5% by mass or less, and further preferably 3% or less in the total amount of solid components from the viewpoint of the viscosity of a film liquid.

Note that in the present invention, the "solid components" are the substances obtained by removing water from the film composition.

The starch in the present invention means unmodified α-1,4-glucan obtained from the seeds, roots, root stocks or the like of higher plants as stored polysaccharides.

In the present invention, the modified starch means starch obtained by adding water and chemicals (various salts, adipic acid, sodium hypochlorite, vinyl acetate, phosphoric acid compounds and the like) to starch if needed and performing heat treatment, ultrasonic treatment, or other treatments. Examples of the modified starch include the below-mentioned waxy corn starch.

The starch or the modified starch used in the present invention is not particularly limited. Examples of the starch or the modified starch used in the present invention include one or more starches selected from natural starch, oxidized starch, hydroxypropylated starch, acetylated starch, starches subjected to acetylation, hydroxypropylation, octenylsuccination, phosphorylation, crosslinking, acid treatment, and moist heat treatment in the presence of a salt, or a starch dispersion obtained by ultrasonically treating a starch paste solution.

The waxy corn starch subjected to moist heat treatment in the presence of a salt is starch obtained by heating waxy corn starch under moist conditions in the presence of a salt. The production can be performed by drying and pulverization after the moist heat treatment if needed.

Such starch is known, and is produced from waxy corn starch, for example, by a method described in Japanese Patent No. 4608051 or a method based on this.

The viscosity of a starch glue solution of the waxy corn starch subjected to moist heat treatment in the presence of a salt (B type viscometer, starch content 40% by mass, solution temperature 90° C.) is preferably 100 to 3000 mPa·s. When the viscosity is 100 mPa·s or more, the "richness" of starch appears, and the film sheet becomes flexible and, easily stretchy, and easily adhere satisfactorily, which is preferable.

The waxy corn starch to be subjected to moist heat treatment is preferably unmodified waxy corn starch, namely waxy corn starch not subjected to acid treatment, pregelatinization, etherification, acetylation or the like.

Waxy potato starch is preferably starch obtained by treating waxy potato starch with acid, and the viscosity of the starch glue solution (starch content 30% by mass, solution temperature 80° C.) is preferably 6 mPa·s or more, and further preferably 10 to 20 mPa·s from a comprehensive viewpoint (the viewpoint of film strength and the viewpoint of gelling strength).

Waxy potato starch may be added instead of waxy corn starch subjected to moist heat treatment in the presence of a salt, or may be added together with waxy corn starch subjected to moist heat treatment in the presence of a salt and/or waxy corn starch subjected to ultrasonic treatment.

The content of waxy corn starch subjected to moist heat treatment in the presence of a salt and waxy potato starch is preferably 1% by mass or more, more preferably 5% by mass or more, and further preferably 10% by mass or more in the total amount of solid components as the total amount thereof. The content is preferably 50% by mass or less, more preferably 40% by mass or less, and further preferably 30% by mass or less in the total amount of solid components from the viewpoint of film sheet strength.

The starch dispersion formed by subjecting the starch glue solution to ultrasonic treatment is a well-known substance, and is produced from starch, for example, by a method described in Japanese Patent No. 4288381 or a method based on this.

The starch glue solution is prepared in a usual method, for example, by heating starch in water or the like and gelatinizing starchiness. Although the content of starch in the starch glue solution is not particularly limited, the content is preferably 1% by mass or more, more preferably 5% by mass or more, and further preferably 10% by mass or more.

Examples of the type of starch include potato starch, tapioca starch, sago starch, sweet potato starch, mung bean starch, wheat starch, corn starch, rice starch, waxy corn starch, waxy potato starch, waxy wheat starch or waxy rice starch; or modified starches obtained from these. These starches and modified starches can be used alone or in combination of two or more. Examples of one embodiment of the starch or the modified starch used in the present invention include one or more starches selected from potato starch, tapioca starch, sago starch, sweet potato starch, mung bean starch, wheat starch, corn starch, rice starch, waxy corn starch, waxy potato starch, waxy wheat starch or waxy rice starch; or modified starches obtained from these. Examples of another embodiment of the starch or the modified starch used in the present invention include one or more starches selected from waxy potato starch, oxidized starch, starch subjected to moist heat treatment in the presence of a salt, or a starch dispersion obtained by ultrasonically treating a starch paste solution.

Note that the starch used for preparing a starch glue solution is preferably unmodified starch, namely modification such as acid subjected to starch not treatment, pregelatinization, etherification, acetylation or the like.

Although the viscosity of the starch glue solution when ultrasonic treatment is performed (B type viscometer, starch content 5% by mass, solution temperature 95° C.) varies depending on the type of starch, the viscosity is preferably 400 to 800 mPa·s, and more preferably 400 to 600 mPa·s.

The conditions of ultrasonic treatment can be optionally set.

The viscosity of the starch glue solution decreases by ultrasonic treatment to obtain a starch dispersion. Although the viscosity (B type viscometer, starch content 20% by mass, solution temperature 80° C.) of the starch dispersion after ultrasonic treatment varies depending on the type of starch, the viscosity is preferably 350 mPa·s or less, and more preferably 10 to 350 mPa·s.

Although the form of the starch dispersion formed by subjecting the starch glue solution to ultrasonic treatment may be liquid, the form of a dried substance obtained by drying this is preferable. Examples of the drying method include spray drying, freeze-drying and evaporation to dryness.

In the present invention, a commercial item of the starch dispersion formed by subjecting the starch glue solution to ultrasonic treatment can also be used.

The content (dry mass, the following are the same) of the starch dispersion formed by subjecting the starch glue solution to ultrasonic treatment is preferably 10% by mass or more, more preferably 20% by mass or more, and further preferably 30% by mass or more in the total amount of solid components from the viewpoint of adhesiveness. The content is preferably 60% by mass or less, and more preferably 50% by mass or less in the total amount of solid components from the viewpoint of film sheet strength.

Other starches can be incorporated into the soft capsule film composition of the present invention besides waxy corn starch subjected to moist heat treatment in the presence of a salt, waxy potato starch and the starch dispersion formed by subjecting the starch glue solution to ultrasonic treatment if needed.

The content of starches other than waxy corn starch subjected to moist heat treatment in the presence of a salt and the starch dispersion formed by subjecting the starch glue solution to ultrasonic treatment is preferably 50% by mass or less, more preferably 40% by mass or less, further preferably 30% by mass or less, and further more preferably 10% by mass or less in the total amount of solid components from the viewpoints of film sheet strength, adhesive force, and elasticity after drying. The lower limit value is 0% by mass.

Examples of the type of such starch include potato starch, tapioca starch, sago starch, sweet potato starch, mung bean starch, wheat starch, corn starch, rice starch, waxy corn starch, waxy potato starch, waxy wheat starch and waxy rice starch. These can be used alone or in combination of two or more.

In the soft capsule film composition of the present invention, a gelling agent other than (A) the native gellan gum and (B) the one or more hydrophilic polysaccharides is not an essential component. Therefore, the soft capsule film composition of the present invention contains only (A) the native gellan gum and (B) the one or more hydrophilic polysaccharides as gelling agents, and may not contain another gelling agent.

The plasticizer is not particularly limited, examples of the plasticizer include sugar alcohols such as glycerin, sorbitol, erythritol, propylene glycol and polyethylene glycol. These may be used alone or as a mixture. Especially, glycerin and sorbitol are preferable.

The content of the plasticizer in the soft capsule film composition of the present invention is preferably 20 parts by mass or more, and more preferably 30 parts by mass or more in the total amount of solid components from the viewpoint of flexibility. The content is preferably 60 parts by mass or less, and more preferably 50 parts by mass or less based on 100 parts by mass of the total amount of solid components from the viewpoint of adhesive properties.

The content of water is preferably 80 parts by mass or more, and further preferably 100 parts by mass or more based on 100 parts by mass of the total amount of solid components. Water to be used is preferably purified water (for example, purified water obtained by passing tap water through ion exchange resin).

Prescriptions of the soft capsule film composition of the present invention, comprising: (A) the native gellan gum; (B) the one or more hydrophilic polysaccharides; (C) the starch or the modified starch; (D) the plasticizer; and (E) the water, wherein a gelling agent other than (A) the native gellan gum and (B) the one or more hydrophilic polysaccharides is not an essential component are illustrated below.

Prescription Example 1

(A) Native gellan gum
(B) Low methoxy pectin
(C) Waxy potato starch
(C) Starch dispersion formed by subjecting starch glue solution to ultrasonic treatment
(D) Glycerin
(E) Purified water Prescription Example 2

(A) Native gellan gum
(B) Low methoxy pectin
(C) Waxy potato starch
(C) Waxy corn starch subjected to moist heat treatment in the presence of salt
(D) Glycerin
(E) Purified water Prescription Example 3

(A) Native gellan gum
(B) Low methoxy pectin
(C) Waxy potato starch
(C) Oxidized starch
(D) Glycerin
(E) Purified water Prescription Example 4

(A) Native gellan gum
(B) Low methoxy pectin
(C) Waxy corn starch subjected to moist heat treatment in the presence of salt
(C) Starch dispersion formed by subjecting starch glue solution to ultrasonic treatment
(D) Glycerin
(E) Purified water Prescription Example 5

(A) Native gellan gum
(B) Locust bean gum
(C) Waxy potato starch
(C) Starch dispersion formed by subjecting starch glue solution to ultrasonic treatment
(D) Glycerin
(E) Purified water Prescription Example 6

(A) Native gellan gum
(B) Locust bean gum
(C) Waxy potato starch
(C) Waxy corn starch subjected to moist heat treatment in the presence of salt
(D) Glycerin
(E) Purified water Prescription Example 7

(A) Native gellan gum
(B) Locust bean gum
(C) Waxy potato starch
(C) Oxidized starch
(D) Glycerin
(E) Purified water Prescription Example 8

(A) Native gellan gum
(B) Locust bean gum
(C) Waxy corn starch subjected to moist heat treatment in the presence of salt
(C) Starch dispersion formed by subjecting starch glue solution to ultrasonic treatment
(D) Glycerin
(E) Purified water Prescription Example 9

(A) Native gellan gum
(B) Xanthan gum
(C) Waxy potato starch
(C) Starch dispersion formed by subjecting starch glue solution to ultrasonic treatment
(D) Glycerin
(E) Purified water Prescription Example 10

(A) Native gellan gum
(B) Xanthan gum
(C) Waxy potato starch
(C) Waxy corn starch subjected to moist heat treatment in the presence of salt
(D) Glycerin
(E) Purified water

Prescription Example 11

(A) Native gellan gum
(B) Xanthan gum
(C) Waxy potato starch
(C) Oxidized starch
(D) Glycerin
(E) Purified water

Prescription Example 12

(A) Native gellan gum
(B) Xanthan gum
(C) Waxy corn starch subjected to moist heat treatment in the presence of salt
(C) Starch dispersion formed by subjecting starch glue solution to ultrasonic treatment
(D) Glycerin
(E) Purified water

Prescription Example 13

(A) Native gellan gum
(B) Low methoxy pectin
(B) Locust bean gum
(C) Waxy potato starch
(C) Starch dispersion formed by subjecting starch glue solution to ultrasonic treatment
(D) Glycerin
(E) Purified water

Prescription Example 14

(A) Native gellan gum
(B) Low methoxy pectin
(B) Locust bean gum
(C) Waxy potato starch
(C) Waxy corn starch subjected to moist heat treatment in the presence of salt
(D) Glycerin
(E) Purified water

Prescription Example 15

(A) Native gellan gum
(B) Low methoxy pectin
(B) Locust bean gum
(C) Waxy potato starch
(C) Oxidized starch
(D) Glycerin
(E) Purified water

Prescription Example 16

(A) Native gellan gum
(B) Low methoxy pectin
(B) Locust bean gum
(C) Waxy corn starch subjected to moist heat treatment in the presence of salt
(C) Starch dispersion formed by subjecting starch glue solution to ultrasonic treatment
(D) Glycerin
(E) Purified water

Prescription Example 17

(A) Native gellan gum
(B) Low methoxy pectin
(B) Xanthan gum
(B) Locust bean gum
(C) Waxy potato starch
(C) Starch dispersion formed by subjecting starch glue solution to ultrasonic treatment
(D) Glycerin
(E) Purified water

Prescription Example 18

(A) Native gellan gum
(B) Low methoxy pectin
(B) Xanthan gum
(B) Locust bean gum
(C) Waxy potato starch
(C) Waxy corn starch subjected to moist heat treatment in the presence of salt
(D) Glycerin
(E) Purified water

Prescription Example 19

(A) Native gellan gum
(B) Low methoxy pectin
(B) Xanthan gum
(B) Locust bean gum
(C) Waxy potato starch
(C) Oxidized starch
(D) Glycerin
(E) Purified water

Prescription Example 20

(A) Native gellan gum
(B) Low methoxy pectin
(B) Xanthan gum
(B) Locust bean gum
(C) Waxy corn starch subjected to moist heat treatment in the presence of salt
(C) Starch dispersion formed by subjecting starch glue solution to ultrasonic treatment
(D) Glycerin
(E) Purified water

Prescription Example 21

(A) Native gellan gum
(B) Low methoxy pectin
(C) Waxy potato starch
(C) Starch dispersion formed by subjecting starch glue solution to ultrasonic treatment
(C) Waxy corn starch subjected to moist heat treatment in the presence of salt
(D) Glycerin
(E) Purified water

Prescription Example 22

(A) Native gellan gum
(B) Low methoxy pectin
(C) Waxy potato starch
(C) Starch dispersion formed by subjecting starch glue solution to ultrasonic treatment
(C) Oxidized starch
(D) Glycerin
(E) Purified water Prescription Example 23

(A) Native gellan gum
(B) Low methoxy pectin
(C) Waxy potato starch
(C) Waxy corn starch subjected to moist heat treatment in the presence of salt
(C) Oxidized starch
(D) Glycerin
(E) Purified water Prescription Example 24

(A) Native gellan gum
(B) Low methoxy pectin
(C) Starch dispersion formed by subjecting starch glue solution to ultrasonic treatment
(C) Waxy corn starch subjected to moist heat treatment in the presence of salt
(C) Oxidized starch
(D) Glycerin
(E) Purified water Various additives such as a natural color, a synthetic color, various sweeteners, an antiseptic, a water activity reducing agent, and a pH adjuster used for soft capsule film compositions can be further incorporated into the soft capsule film composition of the present invention if needed.

A soft capsule is obtained by molding this soft capsule film composition into a predetermined shape and drying the composition. The soft capsule can be produced by a method for producing a soft capsule used conventionally, for example, a punching method or a plate method using a rotary die soft capsule filling machine or the like, for example. Especially the production by a rotary die style is preferable from the viewpoint that the effect of the present invention is exhibited effectively and the viewpoint of industrial productivity. In a rotary die soft capsule filling machine, the molding of a soft capsule and the filling of capsule contents are performed simultaneously by a method in which two film sheets formed by spreading a soft capsule film liquid on rotary drums are punched out in the shape of a capsule by a pair of rotating metallic molds (die rolls).

In the step of spreading the solution of the soft capsule film composition of the present invention on the rotary drums of the rotary die filling machine or the like to form the film sheets, heating the rotary drums at 30 to 80° C. adds mechanical strength and adhesive force for crimping to the film sheets and enables molding a soft capsule having enough strength. The sealing of the contents with the metallic molds at the time of filling the capsule is performed by heating the two film sheets with a segment, resulting in heat sealing; crimping; or the combined use thereof. However, it is desirable that the segment temperature is low from the viewpoint of the protection from heating when a medicine having weak heat resistance or the like is the contents. In the present invention, as shown in the following Examples with a rotary die capsule filling machine, filling and sealing are possible also at room temperature, and adaptation also to such a case can be fully performed.

The shape of the soft capsule is not particularly limited as long as the shape is a shape suitable for oral administration. Examples of the shape include an oval (football) shape, an oblong (long ellipse) shape, a round (spherical) shape, and a special shape such as a tube shape.

The soft capsule produced using the soft capsule film composition of the present invention can be utilized for various uses such as drugs, quasi drugs, cosmetics, and foods, and the composition of the capsule contents is suitably determined depending on the use. The form of the contents may be any of the form of solution, the form of a suspension, the form of paste, the form of powder, the form of a granule and the like.

Substances which can be incorporated into the capsule will be illustrated below. These components can be incorporated into any portions in the capsule.

As oils and fats, avocado oil, almond oil, linseed oil, fennel oil, perilla seed oil, olive oil, olive squalene, orange oil, orange raffer oil, sesame oil, garlic oil, cacao butter, pumpkin seed oil, camomile oil, carrot oil, cucumber oil, beef tallow fatty acid, kukui nut oil, cranberry seed oil, brown rice germ oil, rice bran oil, wheat germ oil, safflower oil, shea fat, liquid shea fat, perilla oil, soybean oil, evening primrose oil, camellia oil, corn oil, rapeseed oil, saw palmetto extract oil, adlay oil, persic oil, parsley seed oil, castor oil, sunflower oil, grape seed oil, borage oil, macadamia nut oil, meadow-foam oil, cottonseed oil, peanut oil, turtle oil, mink oil, yolk oil, fish oil, palm oil, palm kernel oil, Japan wax, coconut oil, a fatty acid triglyceride having long chains, medium chains or short chains, diacyl glyceride, beef tallow, lard, squalene, squalane, pristane, hydrogenated products of these oils and fats, and the like can be contained.

As waxes, shellac wax, beeswax, carnauba wax, spermaceti, lanolin, liquid lanolin, reduced lanolin, hard lanolin, cyclic lanolin, lanolin wax, candelilla wax, Japan wax, montan wax, rice wax or the like can be contained. As hydrogenated oil, vegetable hydrogenated oils, which are obtained by hydrogenating vegetable oils and fats, beef tallow hydrogenated oil, lard hydrogenated oil and the like can be contained.

As mineral oils, liquid paraffin, Vaseline, paraffin, ozokerite, ceresin, microcrystalline wax and the like can be contained.

As fatty acids, natural fatty acids such as lauric acid, myristic acid, palmitic acid, stearic acid, behenic acid, oleic acid, linoleic acid, conjugated linoleic acid, linolenic acid, docosahexaenoic acid, eicosapentaenoic acid, 12-hydroxystearic acid, undecylenic acid, tall oil, and a lanolin fatty acid; synthetic fatty acids such as isononanoic acid, caproic acid, 2-ethylbutanoic acid, isopentanoic acid, 2-methylpentanoic acid, and 2-ethylhexanoic acid; oils and fats containing these fatty acids as fatty acid compositions; and the like can be contained. As vitamins, a vitamin A group: retinol, retinal (vitamin A1), dehydroretinal (vitamin A2), carotene and lycopene (provitamin A); a vitamin B group: fursultiamine, thiamine hydrochloride, thiamin sulfate (vitamin B1), riboflavin (vitamin B2), pyridoxine (vitamin B6), cyanocobalamin, methylcobalamin (vitamin B12), folic acids, nicotinic acids, pantothenic acids, biotins, corrin and inositols; a vitamin C group: ascorbic acid or derivatives thereof; a vitamin D group: ergocalciferol (vitamin D2), cholecalciferol (vitamin D3) and dihydrotachysterol; a vitamin E group: vitamin E or derivatives thereof, and ubiquinones; a vitamin K group: phytonadione (vitamin K1), menaquinone (vitamin K2), menatetrenone, menadione (vitamin K3) and menadiol (vitamin K4); others, essential fatty acid (vitamin F), carnitine, ferulic acid, γ-orizanol, orotic acid, vitamins P (rutin, eriocitrin and hesperidin), vitamin U; and the like can be contained.

As stimulants, capsicum tincture, red pepper oil, nonylic acid vanillylamide, cantharides tincture, ginger tincture, ginger oil, peppermint oil, 1-menthol, camphor, benzyl nicotinate and the like can be contained.

As ultraviolet absorbing and screening agents, benzophenone derivatives (2-hydroxy-4-methoxybenzophenone, 2-hydroxy-4-methoxybenzophenone-5-sulfonic acid, 2-hydroxy-4-methoxybenzophenone-5-sulfonic acid sodium, dihydroxy dimethoxybenzophenone, dihydroxy dimethoxybenzophenone-sulfonic acid sodium, 2,4-dihydroxybenzophenone, tetrahydroxybenzophenone and the like), para-aminobenzoic acid derivatives (para-aminobenzoic acid, ethyl para-aminobenzoate, glyceryl para-aminobenzoate, amyl para-dimethylaminobenzoate, octyl para-dimethylaminobenzoate, and the like), methoxycinnamic acid derivatives (ethyl para-methoxycinnamate, isopropyl para-methoxycinnamate, octyl para-methoxycinnamate, 2-ethoxyethyl para-methoxycinnamate, sodium para-methoxycinnamate, potassium para-methoxycinnamate, di-p-methoxycinnamic acid mono-2-ethylhexanoic acid glyceryl, and the like), salicylic acid derivatives (octyl salicylate, phenyl salicylate, homomenthyl salicylate, dipropylene glycol salicylate, ethylene glycol salicylate, myristyl salicylate, methyl salicylate, and the like), anthranilic acid derivatives (methyl anthranilate and the like), urocanic acid derivatives (urocanic acid, ethyl urocanate, and the like), coumarin derivatives, amino acid-based compounds, benzotriazole derivatives, tetrazole derivatives, imidazoline derivatives, pyrimidine derivatives, dioxane derivatives, camphor derivatives, furan derivatives, pyrone derivatives, nucleic acid derivatives, allantoin derivatives, nicotinic acid derivatives, vitamin B6 derivatives, umbelliferone, esculin, benzyl cinnamate, cinoxate, oxybenzone, dioxybenzone, octabenzone, sulisobenzone, benzoresorcinol, arbutin, guaiazulene, shikonin, baicalin, baicalein, berberine, neoheliopan, escalol, zinc oxide, talc, kaolin, and the like can be contained.

As whitening agents, para-aminobenzoic acid derivatives, salicylic acid derivatives, anthranilic acid derivatives, coumarin derivatives, amino acid-based compounds, benzotriazole derivatives, tetrazole derivatives, imidazoline derivatives, pyrimidine derivatives, dioxane derivatives, camphor derivatives, furan derivatives, pyrone derivatives, nucleic acid derivatives, allantoin derivatives, nicotinic acid derivative, vitamin C or derivatives thereof (a vitamin C phosphate ester magnesium salt, vitamin C glucosides and the like), vitamin E or derivatives or derivatives thereof, oxybenzone, thereof, kojic acid benzophenone, arbutin, guaiazulene, shikonin, baicalin, baicalein, berberine, placenta extract, ellagic acid, rucinol and the like can be contained.

As tyrosinase activity inhibitors, vitamin C or derivatives thereof (a vitamin C phosphate ester magnesium salt, vitamin C glucosides and the like), hydroquinone or derivatives thereof (hydroquinone benzyl ether and the like), kojic acid or derivatives thereof, vitamin E or derivatives thereof, N-acetyltyrosine or derivatives thereof, glutathione, hydrogen peroxide, zinc peroxide, placenta extract, ellagic acid, arbutin, rucinol, silk extract, plant extracts (camomile, mulberries, *Gardenia*, *Angelica acutiloba*, burnet, shrubby sophora, mugwort, Japanese honeysuckle, Amur cork trees, chameleon plant, tuckahoes, tear grass, white dead-nettles, hop, hawthorn, eucalypti, common yarrow, marshmallow, cinnamon, roundleaf chastetree, hamamelis, *Cornus kousa* or *Morus bombycis, Isodon japonicus*, Chinese bellflowers, Cuscutae Semen, caper spurge, *Iris japonica*, mahuangs, *Cnidium officinale*, spikenard, *Bupleurum scorzonerifolium, Siler divaricatum, Glehnia littoralis*, scutellaria root, moutan bark, peony, *Geranium thunbergii*, kudzu roots, licorice, gallnuts, aloe, cimicifuga rhizome, safflower, green tea, black tea, and Gambir), and the like can be contained.

As melanin color-reducing or decomposing substances, phenyl mercury hexachlorophene, mercuric oxide, mercurous chloride, hydrogen peroxide solution, zinc peroxide, hydroquinone or derivatives thereof, and the like can be contained.

As substances having the effect of accelerating turnover and activating cells, hydroquinone, lactic acid bacterium extract, placenta extract, *Ganoderma lucidum* extract, vitamin A, vitamin E, allantoin, spleen extract, thymus extract, yeast extract, fermented milk extract, plant extracts (aloe, scutellaria root, field horsetails, gentian, burdocks, lithospermum roots, carrots, hamamelis, hop, coix seeds, white dead-nettles, swertia, *Angelica acutiloba*, common marigold, sweet hydrangea, St. John's wort, cucumbers, garden thyme, rosemary and parsley), and the like can be contained.

As astringents, succinic acid, allantoin, zinc chloride, zinc sulfate, zinc oxide, calamine, zinc para-phenolsulfonate, aluminum potassium sulfate, resorcin, ferric chloride, tannic acid (containing a catechin compound), and the like can be contained.

As active oxygen scavengers, SODs, catalases, glutathione peroxidase, and the like can be contained.

As antioxidants, vitamin C or salts thereof, stearic acid esters, vitamin E or derivatives thereof, nordihydroguaiaretic acid, butylhydroxytoluene (BHT), butylhydroxyanisole (BHA), hydroxytyrosol, para-hydroxyanisole, propyl gallate, sesamol, sesamolin, gossypol, propolis and the like can be contained.

As lipid peroxide production inhibitors, β-carotin, plant extracts (sesame cultured cells, sweet hydrangea, St. John's wort, hamamelis, clove, melissa, *Isodon japonicus*, white birches, salvia, rosemary, *Nandina domestica* fruits, rose fruits, ginkgo and green tea), and the like can be contained.

As antiinflammatory agents, ichthammol, indomethacin, kaolin, salicylic acid, sodium salicylate, methyl salicylate, acetylsalicylic acid, diphenhydramine hydrochloride, d-camphor, dl-camphor, hydrocortisone, guaiazulene, chamazulene, chlorpheniramine maleate, glycyrrhizic acid or salts thereof, glycyrrhetinic acid or salts thereof, licorice extract, lithospermum root extract, rose fruit extract, propolis and the like can be contained.

As antimicrobial agents, bactericides, and disinfectants, acrinol, sulfur, calcium gluconate, chlorhexidine gluconate, sulfamine, Mercurochrome, lactoferin or a hydrolyzate thereof, alkyldiaminoethylglycine chloride solution, triclosan, sodium hypochlorite, chloramine T, chlorinated lime, iodine compounds, iodoform, sorbic acid or salts thereof, propionic acid or salts thereof, salicylic acid, dehydroacetic acid, para-hydroxybenzoic acid ester, undecylenic acid, thiamine lauryl sulfate, thiamine lauryl nitrate, phenol, cresol, p-chlorophenol, p-chloro-m-xylenol, p-chloro-m-cresol, thymol, phenethyl alcohol, o-phenylphenol, Irgasan CH3565, halocarban, hexachlorophene, chlorhexidine, ethanol, methanol, isopropyl alcohol, benzyl alcohol, ethylene glycol, propylene glycol, 2-phenoxyethanol, 1,2-pentanediol, zinc-pyridione, chlorobutanol, isopropyl methylphenol, nonion surfactants (polyoxyethylene lauryl ether, polyoxyethylene nonyl phenyl ether, polyoxyethylene octyl phenyl ether and the like), amphoteric surfactants, anionic surfactants (sodium lauryl sulfate, lauroyl sarcosine potassium and the like), cationic surfactants (cetyltrimethylammonium bromide, benzalkonium chloride, benzethonium chloride, methylrosanilinium chloride), formaldehyde, hexamine, brilliant green, malachite green, crystal violet, jarmal, the photosensitizer No. 101, the photosensitizer No. 201, the photosensitizer No. 401, N-long-chain acyl basic amino acid derivatives and acid addition salts thereof, zinc oxide, hinokitiol, sophora roots, propolis and the like can be contained.

As humectants, glycerin, propylene glycol, 1,3-butylene glycol, polyethylene glycol, glycerin tricapryl caprylate, glycolic acid (α-hydroxy acid), hyaluronic acid or salts thereof, chondroitin sulfate or salts thereof, water-soluble chitin, derivatives thereof or chitosan derivatives, pyrrolidone carboxylic acid or salts thereof, sodium lactate, urea, sorbitol, amino acids or derivatives thereof (valine, leucine, isoleucine, threonine, methionine, phenylalanine, tryptophan, lysine, glycine, alanine, asparagine, serine, cysteine, cystine, glutamine, tyrosine, proline, hydroxyproline, aspartic acid, glutamic acid, hydroxylysine, arginine, ornithine, histidine; sulfates, phosphates, nitrates and citrates thereof; or pyrrolidone carboxylic acid), and the like can be contained.

As various organic acids, glycolic acid, citric acid, malic acid, tartaric acid, lactic acid, ferulic acid, phytic acid, and the like can be contained.

As agents for hair, selenium disulfide, alkylisoquinolinium bromide liquid, zinc pyrithione, biphenamine, thianthol, casteri tincture, ginger tincture, capsicum tincture, quinine hydrochloride, strong ammonia water, potassium bromate, sodium bromate, thioglycolic acid and the like can be contained.

As perfumes, natural animal perfumes such as musk, civet, castoreum and ambergris; vegetable perfumes such as anise essential oil, angelica essential oil, ylang-ylang essential oil, iris essential oil, fennel essential oil, orange essential oil, cananga essential oil, caraway essential oil, cardamom essential oil, guaiacwood essential oil, cumin essential oil, kuromoji essential oil, cassia essential oil, cinnamon essential oil, geranium essential oil, copaiba balsam essential oil, coriander essential oil, perilla essential oil, cedarwood essential oil, citronella essential oil, jasmine essential oil, ginger-grass essential oil, Japanese cedar essential oil, spearmint essential oil, peppermint essential oil, star anise essential oil, tuberose essential oil, clove essential oil, neroli essential oil, wintergreen essential oil, tolu balsam essential oil, patchouli essential oil, rose essential oil, East Indian geranium essential oil, hinoki essential oil, hiba essential oil, sandalwood essential oil, petitgrain essential oil, bay essential oil, vetiver essential oil, bergamot essential oil, Peru balsam essential oil, rosewood essential oil, *Cinnamomum camphora* var. *nominale* essential oil, mandarin essential oil, *eucalyptus* essential oil, lime essential oil, lavender essential oil, linaloe essential oil, lemon grass essential oil, lemon essential oil, rosemary essential oil, and Japanese mint essential oil; synthetic perfumes such as coffee flavors, and yogurt flavors; and the like can be contained.

The soft capsule is packed in a package form such as a bottling package, a PTP package or a pouch, stored and distributed.

EXAMPLES

Although the present invention will be described specifically hereinafter by giving Examples, the present invention is in no way limited thereto.

The following raw materials were used.

Native gellan gum: KELCOGEL HM (registered trademark) (provided by CP Kelco Japan)

Low methoxy pectin: NEW GELIN (registered trademark) LP-4 (provided by Mitsubishi Shoji Foodtech Co., Ltd.)

Waxy corn starch subjected to moist heat treatment in the presence of salt: Soft Starch SF-930 (provided by Sanwa Starch Co., Ltd.)

Starch dispersion formed by subjecting starch glue solution to ultrasonic treatment: F Smash (registered trademark) (provided by Futamura Chemical Co., Ltd.) (derived from waxy corn starch)

Waxy potato starch: ELIANE GEL 100 (provided by Matsutani Chemical Industry Co., Ltd.)

Glycerin: Food additive grade (provided by Sakamoto Yakuhin Kogyo Co., Ltd.)

Water: Purified water

Examples 1 to 2 and Comparative Examples 1 to 2: Production of Soft Capsule with a Rotary Die Soft Capsule Filling Machine (1) Native gellan gum, low methoxy pectin, waxy corn starch subjected to moist heat treatment in the presence of a salt, a starch dispersion obtained by ultrasonically treating a starch paste solution, waxy potato starch, and glycerin were stirred and dispersed in water in amounts shown in Table 1 (part by mass), respectively, then dissolved with stirring at 90 to 98° C., and vacuum-defoamed. Sheets and a soft capsule were produced from this film liquid using a rotary die soft capsule filling machine.

First, the film liquid was spread on rotary drums with casting devices to prepare the film sheets. In this stage, the following [a. Evaluation of strength of film sheet], [b. Evaluation of stretchiness of film sheet] and [c. Evaluation of stickiness of film sheet] were performed.

(2) Then, the obtained two film sheets were fed between a pair of rotating cylindrical metallic molds through lubricating rollers and deflecting rolls, respectively, encapsulated and molded into an oval (football)-shaped soft capsule. In this stage, [d. Evaluation of adhesiveness of film sheet immediately after molding of capsule] and [e. Evaluation of productivity with capsule filling machine] were performed.

(3) Furthermore, the obtained soft capsule was stored in a desiccator in which the relative humidity was adjusted to 20% or less for 24 hours to obtain a dry soft capsule.

Table 1 shows the results.

[A. Evaluation of Strength of Film Sheet]

The strength of the film sheet was evaluated by the feeling of five special panelists in accordance with the evaluation standard shown below.

5: Very strong
4: Strong
3: Slightly weak
2: Weak
1: Very weak

[b. Evaluation of Stretchiness of Film Sheet]

The stretchiness of the film sheet was evaluated by the feeling of five special panelists in accordance with the evaluation standard shown below at the same time as the evaluation of the strength of the film sheet.

5: The film sheet is very stretchy and elastic.
4: The film sheet is stretchy and elastic.
3: The film sheet is stretchy but has slightly weak elasticity.
2: The film sheet has almost no stretchiness and weak elasticity.
1: The film sheet has no stretchiness and no elasticity.

[c. Evaluation of Stickiness of Film Sheet]

The stickiness of the film sheet was evaluated by the feeling of five special panelists in accordance with the evaluation standard shown below at the same time as the evaluation of the strength of the film sheet.

5: Not sticky
4: Less sticky

3: Slightly sticky
2: Sticky
1: Very sticky

[d. Evaluation of Adhesiveness of Film Sheet Immediately after Molding of Capsule]

Five special panelists crushed capsules before drying with their fingers, and the adhesiveness of the film sheet immediately after the molding of the capsules was evaluated in accordance with the evaluation standard shown below.

5: Even though the capsules are pushed strongly, the content liquid does not leak at all. Even though the capsules are left to stand for 24 hours, leaching does not occur to any capsule.

4: Even though the capsules are pushed strongly, the content liquid does not leak. When the capsules are left to stand for 24 hours, leaching however occurs to some capsules.

3: When the capsules are pushed strongly, a very small amount of the content liquid leaks.

2: Even though the capsules are pushed weakly, a small amount of the content liquid leaks.

1: Even though the capsules are pushed weakly, the content liquid leaks.

[e. Evaluation of Productivity with Capsule Filling Machine]

The productivity with the capsule filling machine was evaluated in accordance with the evaluation standard shown below based on the evaluations of the above-mentioned a to d.

Good: The production with the capsule filling machine using the conventional equipment is possible.

Fair: Although production with the capsule filling machine is possible, the conventional equipment needs to be changed.

Poor: Production with the capsule filling machine is impossible from the physical properties of the film sheet.

TABLE 1

| Test Example | | Example 1 | Example 2 | Comparative Example 1 | Comparative Example 2 |
|---|---|---|---|---|---|
| Prescription | KELCOGEL HM | 8 | 8 | 8 | 8 |
| | NEW GELIN LP-4 | 4 | 4 | — | 4 |
| | Soft Starch SF-930 | — | 30 | — | 44 |
| | F Smash | 68 | 58 | 68 | — |
| | ELIANE GEL 100 | 20 | — | 20 | 44 |
| | Glycerin | 60 | 60 | 60 | 50 |
| | Purified water | 160 | 160 | 160 | 160 |
| | Total | 320 | 310 | 316 | 310 |
| Evaluation | a. Strength | 4 | 4 | 4 | 3 |
| | b. Stretchiness | 4 | 4 | 1 | 3 |
| | c. Stickiness | 3 | 4 | 1 | 3 |
| | d. Adhesiveness | 5 | 5 | 3 | 1 |
| | e. Productivity | Good | Good | Fair | Fair |

As was clear from Table 1, in Comparative Example 1, which does not contain low methoxy pectin, although the strength of the film sheet was high, the film sheet was sticky and unsuitable for production with the capsule filling machine. In Comparative Example 2, which does not contain the starch dispersion formed by subjecting the starch glue solution to ultrasonic treatment, although the film sheet was less sticky, adhesion was weak, and the film sheet was also unsuitable for production with the capsule filling machine.

Meanwhile, in Example 1 and Example 2 according to the present invention, the physical properties of the film sheets were good, and both were easily produced with the capsule filling machine.

Examples 3 to 7 and Comparative Examples 3 to 4: Production of Soft Capsule with Rotary Die Soft Capsule Filling Machine (1) Native gellan gum, low methoxy pectin, locust bean gum, xanthan gum, waxy corn starch subjected to ultrasonic treatment, waxy potato starch, and glycerin were stirred and dispersed in water in amounts shown in Table 2 (part by mass), respectively, then dissolved with stirring at 90 to 98° C., and vacuum-defoamed. Sheets and a soft capsule were produced from this film liquid using a rotary die soft capsule filling machine.

First, the film liquid was spread on rotary drums with casting devices to prepare the film sheets. In this stage, the following [a. Evaluation of strength of film sheet], [b. Evaluation of stretchiness of film sheet] and [c. Evaluation of stickiness of film sheet] were performed.

(2) Then, the obtained two film sheets were fed between a pair of rotating cylindrical metallic molds through lubricating rollers and deflecting rolls, respectively, encapsulated and molded into an oval (football)-shaped soft capsule. In this stage, [d. Evaluation of adhesiveness of film sheet immediately after molding of capsule] and [e. Evaluation of productivity with capsule filling machine] were performed.

(3) Furthermore, the obtained soft capsule was stored in a desiccator in which the relative humidity was adjusted to 20% or less for 24 hours to obtain a dry soft capsule.

Table 2 shows the results.

The standards of the evaluations in Table 2 are the same as the evaluation standards in Table 1 of the "Examples 1 to 2 and Comparative Examples 1 to 2: Production of soft capsule with a rotary die soft capsule filling machine".

TABLE 2

| Test Example | | Example 3 | Example 4 | Example 5 | Example 6 | Example 7 | Comparative Example 3 | Comparative Example 4 |
|---|---|---|---|---|---|---|---|---|
| Prescription | Native gellan gum | 9 | 12 | 12 | 12 | 12 | 9 | — |
| | Low methoxy pectin | 1 | 1 | — | — | 1 | — | 9 |
| | Locust bean gum | — | — | 1 | — | 1 | — | — |
| | Xanthan gum | — | — | — | 1 | — | — | — |
| | Waxy corn starch subjected to ultrasonic treatment | 70 | 67 | 67 | 67 | 66 | 71 | 71 |
| | Waxy potato starch | 20 | 20 | 20 | 20 | 20 | 20 | 20 |

TABLE 2-continued

|  | Test Example | Example 3 | Example 4 | Example 5 | Example 6 | Example 7 | Comparative Example 3 | Comparative Example 4 |
|---|---|---|---|---|---|---|---|---|
|  | Glycerin | 60 | 60 | 60 | 60 | 60 | 60 | 60 |
|  | Purified water | 170 | 170 | 170 | 170 | 170 | 200 | 180 |
|  | Total | 330 | 330 | 330 | 330 | 330 | 350 | 330 |
| Evaluation | a. Strength | 4 | 4 | 4 | 4 | 4 | 4 | 1 |
|  | b. Stretchiness | 4 | 4 | 3 | 4 | 4 | 1 | 1 |
|  | c. Stickiness | 3 | 4 | 4 | 5 | 4 | 1 | 4 |
|  | d. Adhesiveness | 5 | 5 | 5 | 5 | 5 | 3 | 1 |
|  | e. Productivity | Good | Good | Good | Good | Good | Fair | Fair |

INDUSTRIAL APPLICABILITY

A soft capsule film composition of the present invention, comprising: (A) native gellan gum; (B) one or more hydrophilic polysaccharides; (C) starch or modified starch; (D) a plasticizer; and (E) water and not comprising carrageenan enables shortening drying time at room temperature, suppressing the stickiness of the front surface of a film sheet, imparting film sheet strength which enables withstanding continuous production in factory manufacturing with a rotary die filling machine or the like, and manufacturing a good soft capsule with high adhesiveness.

The soft capsule produced using the soft capsule film composition according to the present invention can be utilized for various uses such as drugs, quasi drugs, cosmetics, and foods.

EXPLANATION OF LETTERS OR NUMERALS

10: rotary die capsule filling machine
11: tank
12: casting device
13: rotary drum
14: lubricating roller
15: deflecting roll
16: metallic mold
16A: recess of metallic mold
17: segment
18: pump
18A: piston
A: film sheet
B: contents
C: capsule

The invention claimed is:

1. A soft capsule film composition, comprising: (A) a native gellan gum; (B) one or more hydrophilic polysaccharides selected from low methoxy pectin, locust bean gum and xanthan gum; (C) a starch dispersion formed by subjecting a starch glue solution prepared from an unmodified starch to ultrasonic treatment; (D) a plasticizer; and (E) water, wherein the composition does not comprise a gelling agent other than (A) the native gellan gum and (B) the one or more hydrophilic polysaccharides selected from low methoxy pectin, locust bean gum and xanthan gum, wherein a content mass ratio of (A) the native gellan gum to (C) the starch dispersion formed by subjecting a starch glue solution prepared from an unmodified starch to ultrasonic treatment [(A):(C)] is 1:5.5 to 1:8.5.

2. The soft capsule film composition according to claim 1, further comprising a starch subjected to moist heat treatment in the presence of a salt.

3. The soft capsule film composition according to claim 1, further comprising waxy potato starch.

4. The soft capsule film composition according to claim 1, wherein a content mass ratio of (A) the native gellan gum to (B) the one or more hydrophilic polysaccharides selected from low methoxy pectin, locust bean gum and xanthan gum [(A):(B)] is 1:1 to 1:0.01.

5. The soft capsule film composition according to claim 1, wherein the starch dispersion formed by subjecting a starch glue solution prepared from an unmodified starch to ultrasonic treatment is a starch dispersion derived from waxy corn starch.

6. The soft capsule film composition according to claim 5, wherein the waxy corn starch used for the starch dispersion formed by subjecting a starch glue solution prepared from an unmodified starch to ultrasonic treatment is an unmodified natural starch.

7. The soft capsule film composition according to claim 2, wherein the starch subjected to moist heat treatment in the presence of a salt is waxy corn starch subjected to moist heat treatment in the presence of a salt.

8. A soft capsule film, wherein the soft capsule film is obtained using the soft capsule film composition according to claim 1.

9. A soft capsule, wherein the soft capsule is obtained using the soft capsule film composition according to claim 1.

* * * * *